United States Patent [19]

Houlihan et al.

[11] 3,935,210

[45] Jan. 27, 1976

[54] PREPARATION OF 1-ARYL-4,5-DIHALO-PYRIDAZONE-6

[75] Inventors: William J. Houlihan, Mountain Lakes; Jerome Linder, Westfield, both of N.J.

[73] Assignee: Sandoz, Inc., E. Hanover, N.J.

[22] Filed: May 20, 1974

[21] Appl. No.: 471,462

Related U.S. Application Data

[63] Continuation of Ser. No. 167,481, July 29, 1971, abandoned.

[52] U.S. Cl. ............................................. 260/250 A
[51] Int. Cl.² ........................................ C07D 237/12
[58] Field of Search ............................... 260/250 A

[56] References Cited
FOREIGN PATENTS OR APPLICATIONS
2,033,895  1/1971  Germany ....................... 260/250 A Primary Examiner—Richard J. Gallagher
Assistant Examiner—Anne Marie T. Tighe
Attorney, Agent, or Firm—Gerald D. Sharkin; Richard E. Vila

[57] ABSTRACT

Disclosed is single phase multi-stage process for preparation of 1-aryl-4,5-dihalo-pyridazones-6 involving the diazotization of an amino aryl compound, e.g. aniline, followed by reduction with sulfurous acid to obtain the corresponding aryl hydrazine which is then reacted at elevated temperatures with a mucohalic acid to obtain the 1-aryl-4,5-dihalo-pyridazone-6.

10 Claims, No Drawings

PREPARATION OF 1-ARYL-4,5-DIHALO-PYRIDAZONE-6

This is a continuation of application Ser. No. 167,481 filed July 29, 1971, now abandoned.

This invention relates to the preparation of 1-aryl-4,5-dihalo-pyridazones-6, and more particularly to a new and improved single phase multi-stage process for preparation of such compounds.

Compounds which are 1-aryl-4,5-dihalo-pyridazones-6 are well known and have a variety of uses including use per se as fungicides and use as intermediates in the preparation of other biologically active compounds, e.g. herbicides. Various procedures for preparation of such compounds are also disclosed in the literature as represented by U.S. Pat. Nos. 2,628,181 and 3,045,014. In general, the prior art procedures involve what we defined as at least two reaction phases, i.e. at least one step in which an intermediary product is separated from the liquid reaction medium in which it was formed. In the prior art procedures, the separation may occur at various points in the overall synthesis. In one such procedure an aryl hydrazine is obtained; for example, an amino aryl compound, e.g. aniline, is diazotized and the diazotized product reduced with stannous chloride to obtain the corresponding hydrazine, e.g. phenyl hydrazine, which is separated from the reaction medium in which it is formed prior to being redissolved and reacted with mucohalic acid to form the pyridazone-6. In another procedure the aryl hydrazine may be similarly prepared and retained in solution where it is reacted with a mucohalic acid at about room temperature to obtain an aryl hydrazone which is then separated from the reaction medium prior to being cyclized to obtain the pyridazone-6.

In our own investigations of such prior art procedures involving diazotization and reduction with stannous chloride, we have found that the attempt to convert such procedures to a single phase process resulted, at least, in unattractive yields and complicated purification procedures rendering such trial procedures clearly impractical.

An object of the present invention is to provide a new and improved process for preparation of 1-aryl-4,5-dihalo-pyridazon-6.

Another object is to provide a single phase process for producing 1-aryl-4,5-dihalo-pyridazone-6 starting with a corresponding amino aryl compound.

A further object is to provide a continuous single phase multistage process by which 1-aryl-4,5-dihalo-pyridazones-6 may be efficiently produced in high yield and purity starting with a corresponding amino aryl compound.

These and other objects will be evident from the following description of the invention.

In accordance with the present invention a 1-aryl-4,5-dihalo-pyridazone-6 of the formula I:

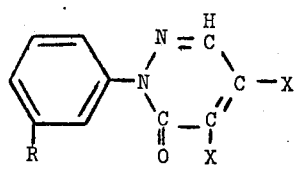

in which R is hydrogen or trifluoromethyl, and X is chloro or bromo, are prepared by reacting an aniline of the formula II:

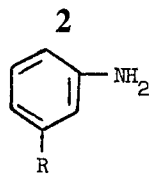

in which R is as above defined, with a diazotization reagent in dilute aqueous mineral acid solution to obtain a dilute aqueous solution of a diazonium salt of the formula III:

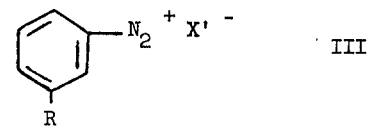

wherein R is as defined and X' is the anionic residue of the mineral acid, said diazonium salt in said dilute aqueous solution then being reacted with sulfurous acid in the presence of a mineral acid to obtain a dilute aqueous solution of a hydrazine acid addition salt of the formula IV:

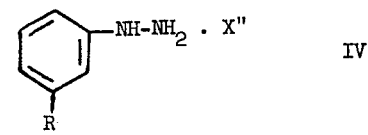

wherein R is as defined and X'' is the mineral acid forming the acid addition salt, and reacting said dilute aqueous hydrazine acid addition salt solution with a mucohalic acid at elevated temperatures to obtain a 1-aryl-4,5-dihalopyridazone-6 of the formula I:

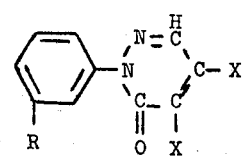

in which R is as defined and X is chloro or bromo.

The reaction of the compound of the formula II with the diazotization reagent to obtain the diazonium salt of the formula III may be considered the first stage of the process of the present invention and is effected in a conventional manner in an aqueous medium at temperatures in the range of from minus 10° to plus 30°C., preferably from minus 5°C. to plus 10°C. The diazotization reagent which is nitrous acid may be formed in situ in a conventional manner from an alkali metal nitrite, preferably sodium nitrite, and the mineral acid used to form the salt of the aromatic amine which is subjected to diazotization. The mineral acid employed may be sulfuric acid or hydrochloric acid, desirably hydrochloric acid. Accordingly, the preferred compounds of the formula III are the aromatic diazonium chlorides. If desired, the aqueous solution containing the resulting aromatic diazonium salt of the formula III may be treated with a scavenger such as urea to take up excess nitrous acid following the diazotization. The resulting aromatic diazonium salt of the formula III is maintained in the aqueous solution in which it is formed for use in the next stage in which the diazonium salt is reduced to the hydrazine.

The resulting aromatic diazonium salt of the formula III in the aqueous solution in which it is formed is then subjected to reduction with sulfurous acid to obtain the aromatic hydrazine acid addition salt of the formula IV. Prior to or at the time of commencing such reduction the aqueous solution of the diazonium salt may be further dilute with water to further protect against rapid decomposition of the type to which diazonium salts are known to be subject. The sulfurous acid is conveniently prepared in situ by bubbling sulfur dioxide into the acidic aqueous solution or by the addition of an alkali metal sulfite or hydrosulfite such as sodium sulfite to such acidic solution. Preferably, the sulfurous acid is provided by in situ preparation by the addition of sodium sulfite. In general, sufficient material is added to provide a substantial excess of the sulfurous acid, desirably at least a 10% excess, preferably an excess of 20% to 100%. Excess amounts greater than 200% provide no additional advantages and only undesirably increase the excess amounts which must be later removed. The reduction reaction is initiated and may be completed at temperatures in the range of from minus 10° to plus 35°C., preferably 0° to 10°C. in the presence of the sulfurous acid and may be largely completed in a relatively short time at such temperatures, for example, over a period of from 15 minutes to 2 hours during the controlled addition of sodium sulfite. In general, the reduction is initiated in a dilute acidic aqueous medium having a pH of from about pH 1.0 to 5.0, more usually pH 1.0 to 4.0. The hydrazine produced by the reduction is a basic material so that the pH of the reaction mixture increases during its formation and, depending upon pH at the time of initiation, may achieve a pH of almost pH 7 at or near the completion of the reduction, provided, however, that the pH is controlled or regulated to maintain the hydrazine product in the form of its acid addition salt and thereby avoid separation of the water insoluble free base from the aqueous reaction mixture. If desired, the reduction temperature may be increased to an intermediary temperature as high as about 60°–70°C. for a short time in order to insure completion of the conversion of the compound III to the aromatic hydrazine of the formula IV, provided, however, that any such heating is desirably effected when the pH of the reaction mixture is above about pH 5.0 to avoid the substantial loss of the sulfurous acid reducing agent in the form of liberated sulfur dioxide. The resulting product is the aromatic hydrazine acid addition salt of the formula IV in aqueous solution and such solution of said product is employed without separation of the product therefrom in the formation of the pyridazone-6 in the final stage of the multi-stage process of the present invention.

The preparation of the pyridazone-6 of the formula V is effected at elevated temperatures by reaction of the aromatic hydrazine acid addition salt of the formula IV with a mucohalic acid in an acidic aqueous medium. It has been postulated that the ability of the process of the invention to operate in a single phase to efficiently produce the pyridazone-6 of the formula V in high yield is dependent upon the substantial removal of the reducing agent from the reaction medium before the formation of the pyridazone-6 has progressed to near completion, desirably before such formation has progressed to the point about 50% of the hydrazine has been converted to the pyridazone-6. As the sulfurous acid reducing agent contains a readily volatilizable component, i.e. sulfur dioxide, it will be evident that such reducing agent may be readily removed from the system by increasing the temperature of an acidic aqueous medium which contains such sulfurous acid.

The final reaction stage involving the preparation of the pyridazone-6 may be carried out in one or more steps defined by the addition of necessary or desired reactants. Both the preparation of the pyridazone-6 and the liberation of sulfur dioxide are effected in an acidic aqueous solution which is more acidic than that preferably remaining after the preparation of the hydrazine. In general, the preparation of the pyridazone-6 is effected in the acidic aqueous solution at a temperature in the range of at least 70° up to 120°C., preferably 90° to 110°C. While the preparation of the pyridazone-6 may be carried out under subatmospheric or superatmospheric pressure conditions, it is most preferably carried out at the reflux temperature of the aqueous reaction mixture at about atmospheric pressure.

The heating to effect the removal of the reducing agent by the liberation of the sulfur dioxide may be effected either before, during or after the addition of the mucohalic acid. In general, the rate of removal of the reducing agent by its liberation in the form of sulfur dioxide is largely a function of time, temperature and acidity of the aqueous mixture containing the reducing agent, the lower temperatures and less acidic systems requiring the longer times. As a practical matter, effective liberation requires a temperature of at least 40°C. and a pH not exceeding pH 5.0. In the more preferred embodiments the sulfur dioxide is rapidly eliminated by heating at a temperature in the range of from 60° to 120°C. with the aqueous system at a pH of pH 2.5 or below, usually in the range of from pH 0.1 to pH 2.5, for a minimum period of time of at least about 10 to 80 minutes, the minimum time within such range for effective removal of the sulfurous acid varying approximately inversely with the temperature and acidity of the solution. The rapid liberation of the sulfur dioxide from the aqueous system tends to result in foaming which may be undesirably excessive and for this reason it is preferred to first heat the aqueous solution at the desired pH in the range of pH 0.1 to pH 2.5 to an intermediary temperature of from 60° to 85°C. in order to effect a more controlled liberation of the sulfur dioxide. While excess sulfurous acid may be effectively removed by heating for the relatively short periods indicated at such intermediary temperatures, it is generally desirable to further heat the aqueous system at the desired pH range of pH 0.1 to pH 2.5 at a temperature of 90° to 120°C. for an additional short period of about 10 minutes to insure the effective removal of the sulfurous acid.

Hence, in a particular embodiment, the removal of the sulfurous acid is effected by heating of the aqueous solution containing the hydrazine acid addition salt prior to the addition of the mucohalic acid. In carrying out such embodiment, the pH of the aqueous solution is regulated or adjusted to the desired level by the use of a mineral acid, i.e. sulfuric acid or hydrochloric acid, and is preferably adjusted to from pH 0.1 to pH 2.5, more preferably between pH 0.2 and pH 1.5, by the addition of hydrochloric acid. The resulting aqueous solution at the pH between pH 0.1 and pH 2.5 is then heated at 60° to 85°C. for a minimum time of at least 15 to 80 minutes to evolve the sulfur dioxide component of the sulfurous acid. In a more typical embodiment, the solution at pH 0.2 to pH 1.5 is heated at 60° to 85°C. for a minimum time of from about 15 minutes to 40 minutes, the actual heating time being preferably from about 30 to 90 minutes. The temperature of the aqueous system is then desirably elevated to within the range of from 90° to 120°C. for an additional period of about 10 minutes to insure effective removal of the sulfur dioxide, although it will be evident that such last indicated heating may be carried out for extended time periods or may be effected after addition of the mucohalic acid when the preparation of the pyridazone-6 is to be carried out within the higher temperature range of from 90° to 120°C.

In another particular embodiment the removal of the sulfurous acid is effected by heating of the aqueous solution containing the hydrazine acid addition salt after the addition thereto of the mucohalic acid. In carrying out the invention in this manner it is important that the aqueous solution have a pH in the range of from pH 0.1 to pH 2.5 before any substantial period of heating at the temperatures at which the reaction of the hydrazine with the mucohalic acid takes place, i.e. 70° to 120°C., in order to insure that effective removal of the sulfur dioxide is achieved well before completion of the reaction forming the pyridazone-6. While the addition of the mucohalic acid effects an increase in the acidity of the solution containing the hydrazine acid addition salt it is usually necessary when carrying out the process under preferred conditions to add additional acid in order to obtain a pH within the necessary range. Such addition as required is effected by adding sulfuric or hydrochloric acid in concentrated form, preferably hydrochloric acid, e.g. 35% hydrochloric acid, until the pH is within the sought for range. In a more specific embodiment the mucohalic acid and mineral acid as required to obtain a pH of from pH 0.1 to pH 2.5 are added to the aqueous solution containing the hydrazine acid addition salt and the resulting solution heated to an intermediary temperature of from 60° to 85°C. for a minimum of 15 to 80 minutes, more preferably at pH 0.2 to pH 1.5 for a minimum of from 15 to 40 minutes, the actual heating time being preferably from about 30 to 90 minutes. The preparation of the pyridazone-6 is then preferably completed by heating within the preferred temperature range of from 90° to 110°C., more preferably the reflux temperature, for an additional period of time of usually 30 minutes to 5 hours, more typically 1 to 3 hours.

As stated, the preparation of the pyridazone-6 is effected in acidic aqueous solution at a temperature in the range of at least 70°C. up to 120°C., the reaction proceeding with desirably efficiency at temperature of at least 90°C. such that the reaction is preferably conducted in the range of 90° to 110°C., more preferably 100° to 110°C. The mol ratio of the mucohalic acid to the hydrazine acid addition salt as a practical matter is within the range of from 0.8:1 to 1.5:1, preferably about 1:1 to 1.3:1. The reaction has been observed to proceed through the hydrazone intermediate and for this reason the reaction is carried out with agitation, e.g. vigorous stirring, in order to maintain the water insoluble hydrazone in the aqueous reaction medium.

The reaction of the hydrazine acid addition salt with the mucohalic acid in the process of the invention produces the pyridazone-6 in high yields of the order of at least about 85%, more usually of the order at least about 90%. Overall yields for the process commencing with the aniline of the formula II are generally of the order of at least about 80%, more usually at least about 85%. In addition to high yields the process operates without substantial formation of undesired by-products and the pyridazone-6 final product may be readily obtained with a purity of at least about 90%, more usually at least 95%, the only substantial factor bearing on purity being the purity of the starting aniline of the formula II itself to the extent that the desired starting aniline contains another aniline which is subject to reaction in the process.

The following examples illustrate the process of the invention and advantages thereof and are for purposes of illustration only.

EXAMPLE 1

To a mixture consisting of 270 g. ice and 161 ml. of concentrated hydrochloric acid is added 86.6 g. trifluoromethyl-m-toluidine while maintaining the reaction temperature at 0°–10°C. To the resulting mixture is added a solution consisting of 39 g. sodium nitrite in 376 ml. water at 0°C. The reaction mixture is then stirred for 15 minutes at 0°C. and there is then added 26.8 g. urea followed by stirring for 30 minutes at 0°C. The resulting product solution is added to a solution consisting of 204 g. sodium sulfite in 900 ml. of water and the resulting solution stirred at a temperature of 5°–10°C. for thirty minutes and then heated at 60°C. for 1 hour. There is then added 175 ml. of concentrated (35%) hydrochloric acid and the reaction mixture heated to 60°–70°C. for 30 minutes during which sulfur dioxide is evolved. The reaction mixture is then refluxed for 3 hours (temperature about 100°–110°C), and then 98 g. of mucohalic acid is added and the resulting mixture refluxed (100°–110°C.) with stirring for 3 hours. The reaction mixture is cooled to room temperature and filtered to obtain 161 g. 1-(3-trifluoromethylphenyl)-4,5-dichloropyridazone-6, m.p. 90°–93°C.

EXAMPLE 2

To a mixture consisting of 270 g. of ice and 116 ml. of concentrated hydrochloric acid is added 50 g. of aniline while maintaining the reaction temperature at 0°–10°C. To the resulting mixture is added a solution consisting of 39 g. sodium nitrite in 376 ml. of water at 0°C. The reaction mixture is then stirred for 15 minutes at 0°C. and there is added 13.4 g. urea and stirring continued for 30 minutes at 0°C. This product solution is added to a solution consisting of 204 g. sodium sulfite in 900 ml. of water and the resulting solution is stirred at a temperature of 5°–10°C. for thirty minutes, and then heated at 60°C. for one hour. To the resulting mixture is added 175 ml. of concentrated (35%) hydrochloric acid and the reaction mixture heated to 60°–70°C. for 30 minutes during which sulfur dioxide is evolved. The reaction mixture is then refluxed for 3 hours (temperature about 100°–110°C.), and then 98 g. of mucochloric acid is added and the mixture refluxed (100°–110°C.) for 3 hours. The reaction mixture is then cooled to room temperature and filtered to obtain 117 g. of 1-phenyl-4,5-dichloro-pyridazone-6, m.p. 159°–161°C.

EXAMPLE 3

To a mixture consisting of 160 g. of ice and 70 ml. of concentrated (35%) hydrochloric acid is added 53.2 g. of trifluoromethyl-m-toluidine while maintaining the temperature at 0°–5°C. To the resulting mixture is added a solution consisting of 24 g. of sodium nitrate in 100 ml. water at 0°C. The reaction mixture is then stirred for 15 minutes at 0°C. and is then added over a period of one hour to a solution consisting of 130 g. of sodium sulfite in 250 ml. of water and having a temperature of 30°C. The resulting solution is stirred for 20 minutes at 30°C. and there is then added over the course of 1 hour 100 ml. of concentrated (35%) hydrochloric acid and 51.0 g. of mucochloric acid. The resulting solution is heated with stirring at 80°C. for 1 hour and then refluxed (100°–110°C.) with stirring for 2 hours. The reaction mixture is cooled to room temperature and filtered to obtain 1-(3-trifluoromethylphenyl)-4,5-dichloro-pyridazone-6, m.p. 90°–93.5°C.

What is claimed is:

1. A single aqueous phase process for preparation of a 1-aryl-4,5-dihalopyridazone-6 comprising the steps of: a) reacting a compound of the formula:

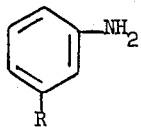

in which R is hydrogen or trifluoromethyl with nitrous acid in a dilute aqueous solution in the presence of a mineral acid selected from the group consisting of hydrochloric acid and sulfuric acid to obtain a dilute aqueous solution of a diazonium salt of the formula:

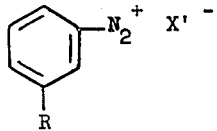

in which R is as defined above and X' is the anionic residue of the mineral acid; b) maintaining said diazonium salt in the aqueous solution in which it is formed and reacting said diazonium salt with excess sulfurous acid in the presence of a mineral acid selected from the group consisting of hydrochloric acid and sulfuric acid at a temperature in the range of from minus 10° to plus 35°C. to obtain a dilute aqueous solution of a hydrazine acid addition salt of the formula:

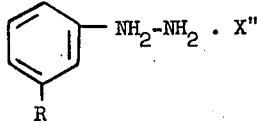

in which R is as above defined and X" is the mineral acid forming the acid addition salt; and c) maintaining said hydrazine acid addition in the aqueous solution in which it is formed, regulating the acidity of said aqueous solution at a pH not exceeding pH 5.0, heating said aqueous solution at a pH not exceeding pH 5.0 to a temperature of at least 40°C. to remove excess sulfurous acid in the form of sulfur dioxide and reacting said hydrazine acid addition salt with mucochloric or mucobromic acid in the aqueous solution in which the hydrazine is formed at a temperature of from 70° to 120°C. to obtain a 1-aryl-4,5-dihalopyridazone-6 of the formula:

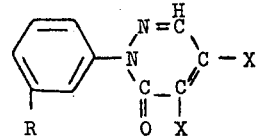

in which R is as above defined and X is chloro or bromo.

2. The process of claim 1 in which the hydrazine is reacted with mucochloric acid.

3. The process of claim 2 in which the hydrazine acid addition salt solution is heated to remove sulfurous acid at a temperature of from 60° to 85°C. at a pH of from pH 0.1 to pH 2.5.

4. The process of claim 3 in which the hydrazine acid addition salt solution is heated to remove sulfurous acid at a temperature of from 60° to 85°C. for at least 15 minutes in the absence of mucochloric acid and in which said solution is subsequently further heated at a temperature of from 90° to 120°C. for at least 10 minutes.

5. The process of claim 4 in which said subsequent heating in the range of from 90° to 120°C. is effected in the absence of mucochloric acid.

6. The process of claim 3 in which the hydrazine acid addition salt solution is heated to remove sulfurous acid at a temperature of from 60° to 85°C. for at least 15 minutes in the presence of mucochloric.

7. The process of claim 6 in which the solution is heated to a temperature of from 90° to 120°C. subsequent to said heating at from 60° to 85°C. to obtain said 1-aryl-4,5-dihalopyridazone-6.

8. The process of claim 4 in which the pH is regulated by the addition of hydrochloric acid and in which R is trifluoromethyl.

9. The process of claim 7 in which the pH is regulated by the addition of hydrochloric acid and in which R is trifluoromethyl.

10. The process of claim 4 in which the pH is regulated by the addition of hydrochloric acid and in which R is hydrogen.

* * * * *